United States Patent [19]

Zeiss

[11] Patent Number: 4,922,006
[45] Date of Patent: May 1, 1990

[54] PROCESS FOR THE PREPARATION OF L-PHOSPHINOTHRICINE (DERIVATIVES) AND ALSO OF THEIR ALKYL ESTERS

[75] Inventor: Hans-Joachim Zeiss, Sulzbach, Fed. Rep. of Germany

[73] Assignee: Hoechst Aktiengesellschaft, Frankfurt am Main, Fed. Rep. of Germany

[21] Appl. No.: 28,231

[22] Filed: Mar. 20, 1987

[30] Foreign Application Priority Data

Mar. 22, 1986 [DE] Fed. Rep. of Germany ....... 3609818

[51] Int. Cl.$^5$ ............................. C07F 9/30; C07F 9/32
[52] U.S. Cl. ...................................... 562/11; 558/145
[58] Field of Search ........................... 558/145; 562/11

[56] References Cited

PUBLICATIONS

Suzuki et al., "Chem. Abst.", vol. 93 (1980), 93:46824v.

*Primary Examiner*—Anton H. Sutto
*Attorney, Agent, or Firm*—Curtis, Morris & Safford

[57] ABSTRACT

The process for the preparation of L-phosphinothricine (derivatives) by homogeneous asymmetric hydrogenation of 2,3-dehydrophospinothricine (derivatives) by means of suitable ruthenium, rhodium or iridium catalysts.

8 Claims, No Drawings

PROCESS FOR THE PREPARATION OF L-PHOSPHINOTHRICINE (DERIVATIVES) AND ALSO OF THEIR ALKYL ESTERS

The present invention relates to a process for the preparation of L-homoalanin-4-yl(methyl)phosphinic acid and its derivatives of the general formula I

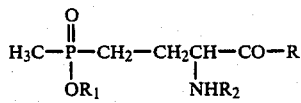

wherein
R denotes hydroxy, $(C_1-C_6)$alkoxy, Ala-Ala(OH) or Ala-Leu(OH),
$R^1$ denotes hydrogen or $(C_1-C_6)$alkyl, and
$R_2$ denotes hydrogen, an acyl, alkoxycarbonyl or aryloxycarbonyl radical
and also salts thereof formed with inorganic or organic acids or bases.

As described in German Offenlegungsschrift 2,856,260, L-homoalanin-4-yl(methyl)phosphinic acid, termed L-phosphinothricine or L-Ptc for short below, its esters and also its salts formed with organic or inorganic acids or bases are the active enantiomers of the herbicidally active racemates described in German Offenlegungsschrift 2,717,440. According to German Offenlegungsschrift 2,856,260, the herbicidal action of L-Ptc against numeraous monocotyledonous and dicotyledonous, annual and biennial weeds is twice as high as that of the racemate. The quantity of the herbicide used can therefore be considerably reduced by using pure L-Ptc instead of the racemate, as a result of which any undesirable side effects are also correspondingly reduced.

An obstacle to the widespread use of L-Ptc, however, has hitherto been the difficulties in preparing it.

Although the acidic or enzymatic cleavage of the antibiotic SF-1293, which contains L-Ptc, is described in the Japanese Preliminary Published Application. 73-85538 and Japanese Preliminary Published Application No. 74-31890, the preparation of the latter by a fermentative route, as is described, for example, in German Offenlegungsschrift 2,236,599, is very expensive.

The cleavage of N-acylated D,L-Ptc derivatives by means of acylases, be it (a) by means of microbial acylases according to German Offenlegungsschrift 2,939,269 or be it (b) by using penicillin-G acylase according to German Offenlegungsschrift 3,048,612 is further known. Disadvantageous in the process (a) is the low optical purity of the L-Ptc obtained, and in (b)—the expensive working up of the crude product using ion exchangers and also the relatively high cost of the phenylacetic acid needed for the acylation.

The only non-enzymatic process for preparing L-Ptc which has hitherto become known and which is described in European Published Application 127,429, uses a chiral, non racemic imine as starting material to construct the chiral carbon atom in L-Ptc in an alkylation step based on the principle of asymmetric induction (for an explanation of the term see E. L. Eliel: Stereochemie der Kohlenstoffverbindungen (Stereochemistry of Carbon Compounds) pages 23–30, published by Verlag Chemie, Weinheim 1966).

Disadvantageous is this process, however, is the fact that the expensive chiral auxiliary substance, which is used to prepare the chiral imine, is required in equimolar quantities and cannot be recovered again after the reaction.

The object therefore existed of developing a simple process which makes possible the preparation of L-phosphinothricine in fairly large quantities and with high optical purity.

The subject of the invention is therefore a process for the preparation of L-homoalanin-4-yl(methyl)phosphinic acid and also its derivatives of the general formula I comprising hydrogenating 2,3-dehydrophosphinothricine derivatives of the general formula II

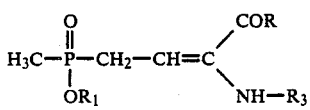

wherein
R and $R_1$ have the same meaning as in formula I and
$R_3$ denotes an acyl, alkoxycarbonyl or aryloxycarbonyl radical, in the presence of a complex of the formula III

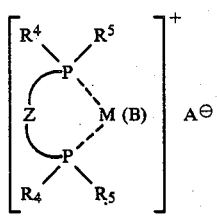

which is suitable for homogeneous asymmetric hydrogenation, and the compounds obtained are optionally saponified, where, in formula III,
Z denotes a $C_2-C_4$-paraffin chain, which may contain one or more substituents or may be part of a ring system,
$R^4$ and $R^5$ are the same or different and denote phenyl or substituted phenyl,
M denotes ruthenium, rhodium or iridium and
B denotes an olefin or diolefin forming a cationic metal coordination complex with M, with the proviso that at least one of the P atoms and/or the radical Z must be chiral, and
$A^-$ is an anion equivalent.

The starting materials II can be prepared, analogously to European Published Application 30,424, in a simple manner from 4-(hydroxymethylphosphinyl)-2-oxobutyric acid and carboxylic acid amides.

In formula II, R preferably stands for OH and $(C_1-C_6)$alkoxy and $R_1$ preferably for H and $(C_1-C_6)$alkyl. $R_3$ is any acyl, alkoxy or aryloxy radical. For practical reasons, the lower alkanoyl (preferably acetyl) and the benzoyl compound(s) are most suitable, but the nature of the radical $R_3$ is not critical for the success of the reaction.

Although hydrogenations with chiral catalysts are known in principle from the literature, high optical yields are always only obtained, as described in German Offenlegungsschrift 2,456,937, if the substituent Q in the starting substances of the general formula IV is an aromatic, or as described in J. Org. Chem. 46, 5086 (1981), an aliphatic radical without functional groups:

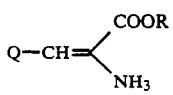  IV

A surprising feature of the novel process is, however, the fact that as substrates for the hydrogenation it is also possible to use those compounds of the general formula IV which carry in their side chain Q a phosphinyl group which is capable of coordinative bonding at the central metal atom of the catalyst and would therefore poison the catalyst.

The novel process is performed in a manner such that the 2,3-dehydrophosphinothricine derivative of the general formula II is dissolved in a suitable solvent such as water, methanol, ethanol, benene, toluene or tetrahydrofuran, under an inert gas atmosphere, inert gases being understood to mean nitrogen or argon, and then a solution of the catalyst in the same or in another solvent is added.

The preparation of the catalyst III is performed in a manner known per se by reacting a complex of the general formula $[(B)M^+A^\ominus]_2$ obtained by reaction of a suitable ruthenium, rhodium or iridium salt with a (di)olefin, either directly or indirectly via the fluoroborate, with a compound of the formula

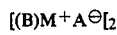  V

These processes are described, for example, in JACS 93, 3089 (1971), J. Org. Chem. 44, 3741 (1979) and also German Auslegeschrift 2,456,937.

Examples of suitable salts are the tribromides, trichlorides or sulphates of Ru, Rh or Ir. Suitable as (di)olefins are ethylene, propylene and butadiene, and their homologs, in particular, however, 1,5-cyclooctadiene and norbornadiene.

An example of the radical Z is the dimethylene radical (—CH₂—CH₂—), which may also carry further substituents, for example, one or two CH₃ groups or the cyclohexyl radical, on one or both CH₂ groups, as a result of which the carbon atom concerned becomes a chirality center. Such compounds are described, for example, in JACS 100, 5491 (1978), Berichte 113, 2323 (1980) and J. Org. Chem. 45, 5187 (1980). Typical representatives are, for example:

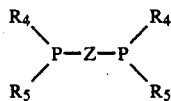  Va

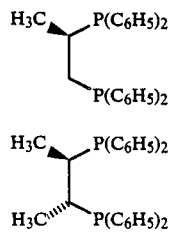  Vb and

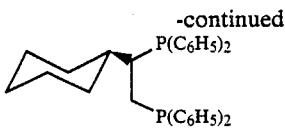  Vc

If the dimethylene radical is unsubstituted, at least one of the two P atoms must be chiral instead, which is the case if the radicals R₄ and R₅ are different from each other. Compounds of this type are described in detail in German Auslegeschrift 2,456,937. A suitable representative of this class of compound is, for example,

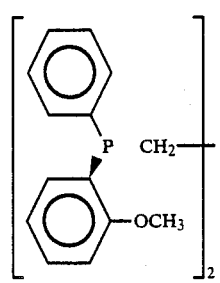  Vd

Compounds of formula V in which the dimethylene radical Z is part of a heterocyclic system are the subject of European Published Application 151,252 and, in addition, are described in Angew. Chem. 96, 425 (1984). The compounds mentioned therein are derived from pyrrolidine and have the general formula

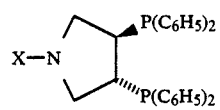  Ve wherein X is an alkyl, aralkyl or acyl radical. A particularly suitable compound is the one in which X represents the benzoyl radical.

Furthermore, the dimethylene radical Z may also be a constituent of an isocyclic ring system. As examples mention may be made of

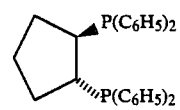  Vf and

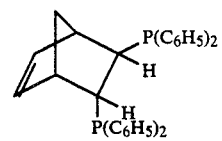  Vg (Vf: J. Chem. Soc. Chem. Comm. 1983, 895; Vg: Berichte 114, 1137 (1981))

Finally, Z may also be a tetramethylene radical (—CH₂—CH₂—CH₂—CH₂—) which is substituted at one or more carbon atoms (preferably thee two middle ones) by a methoxy group. Especially preferred are those compounds in which the two middle carbon atoms are linked to a 5-member or 6-member ring via an O-alkylene-O bridge. Compounds of this type are described in the German Auslegeschrift 2,161,200.

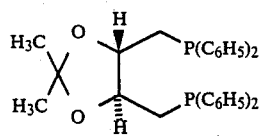

The anion A follows automatically from the preparation process for the complex III described further above. Preferably A is $Cl^-$, $Br^-$, $ClO_4^-$, $BF_4^-$ or $PF_6^-$.

The catalyst can be used either in isolation or in situ for the hydrogenation.

After adding the catalyst to the substrate solution, hydrogen is introduced under pressure. Hydrogenation is carried out at pressures of 0.5–200 bar, preferably, however, at 1–70 bar. The reaction temperature is $-10°$ to $120°$ C., preferably, however, $5°$ to $80°$ C.

The molar ratio of catalyst (III) and substrate (II) is in the range between 1:10 and 1:100,000, preferably, however, in the range between 1:50 and 1:50,000.

After the calculated quantity of hydrogen had been absorbed, the reaction vessel is depressurized and the catalyst is removed in a known manner, for example, by stirring in a cation exchanger.

The N-acyl or alkoxy(phenoxy)carbonyl derivatives produced can be converted by acidic hydrolysis into the amine hydrochlorides ($R_2=H$) and these in turn, as described, for example, in German Offenlegungsschrift 3,048,612, into the free amines. In the case of $R=R_1=H$, the L-Ptc is obtained in this manner in an optical yield of at least 85%, i.e. at least 92%.

The examples below are intended to explain the pprocess in more detail without any restriction being intended.

EXAMPLE 1

L-homoalanin-4-yl(methyl)phosphinic acid (a) 18.0 g (0.1 mol) of 4-(hydroxymethylphosphinyl)-2-oxobutyric acid (prepared according to European Published Application 30,424) and 11.8 g (0.2 mol) of acetamide are suspended in 50 ml of glacial acetic acid and stirred for 4 hours at room temperature. Then 100 ml of toluene and 1 crystal of toluene sulfonic acid are added and the reaction mixture heated for 5 hours under a water separator. The solvent is completely distilled off in vacuo and the residue crystallized by taking it up in glacial acetic acid/toluene. After recrystallization from glacial acetic acid/acetone, 13.1 g (59% of theory) of 2-acetamido-4-(hydroxymethylphosphinyl)-2-butenoic acid are obtained as a white solid with a melting point of 186°–189° C. (decomposes).

(b) 0.0087 g (0.019 mmol) of chloronorbornadienerhodium(I) dimer and 0.022 g (0.053 mmol) of the compound Va are dissolved in 5 ml of methanol under an atmosphere of argon. The catalyst solution obtained is added under argon to a solution of 2.21 g (0.01 mol) of 2-acetamido-4-(hydroxymethylphosphinyl)-2-butenoic acid in 45 ml of methanol. The reaction vessel is evacuated, then hydrogenation is performed at a pressure of 3.0 bar. After a reaction time of 44 hours, the reaction vessel is depressurized, the reaction mixture evaporated down, the residue taken up in water and the precipitated catalyst separated off. As a result of adding an equivalent quantity of concentrated hydrochloric acid to the filtrate, a 6N hydrochloric acid solution is prepared which is boiled under reflux for 12 hours. After evaporating this solution down, 2.0 g (91.9% of theory) of L-homoalanin-4-yl(methyl)phosphinic acid hydrochloride is obtained as a white solid which is purified by recrystallization from an ethanol/water mixture.

Mp. 194°–196° C. (decomposes); $[\alpha]_D^{22}=20.8°$ (c=2.47 in 1N HCl)

(c) 0.33 g (0.0015 mol) of L-homoalanin-4-yl(methyl)phosphinic acid chloride are dissolved in 15 ml of ethanol/water and mixed with 0.3 g (0.005 mol) of propeneoxide. After allowing to stand for one day at room temperature, 0.22 g (80.1% of theory) of L-homoalanin-4-yl(methyl)phosphinic acid is obtained as a white solid with a melting point of 212°–214° C. (decomposes); $[\alpha]_D^{22}=14.7°$ (c=0.984 in $H_2O$).

This corresponds to an optical yield of at least 86.0% relative to $[\alpha]_D^{23}=17.0°$ (c=1 in 1 $H_2O$) for optically pure L-homoalanin-4-yl(methyl)phosphinic acid (Sci. Reports of Meiji Seika Kaisha 13, 42 (1973)).

EXAMPLE 2

L-homoalanin-4-yl(methyl)phosphinic acid hydrochloride (a) 2.21 g (0.01 mol) of 2-acetamido-4-(hydroxymethylphosphinyl)-2-butenoic acid (Example 1a) are dissolved in 60 ml of methanol. A solution of 0.025 g (0.036 mmol) of norbornadiene-[R-(+)-1,2-bis(diphenylphosphino)propane]rhodium tetrafluoroborate (prepared according to JACS 100, 5491 (1978)) in 10 ml of methanol are added to this solution under argon. The reaction vessel is heated to 45° C., then evacuated and hydrogenation is subsequently carried out at a pressure of 1 bar. After a reaction time of 22 hours, the reaction vessel is depressurized and the reaction mixture mixed with 2 g of acidic ion exchanger ($H^+$ form) to remove the catalyst. After stirring for 3 hours at room temperature, the ion exchanger is separated off, the reaction mixture is evaporated down, the residue is taken up in 6N hydrochloric acid and boiled for 12 hours under reflux. After evaporating this solution down, 2.05 g (94.2% of theory) of L-homoalanin-4-yl(methyl)phosphinic acid hydrochloride is obtained as a white solid.

Mp. 188°–190° C. (decomposes).

EXAMPLE 3

L-homoalanin-4-yl(methyl)phosphinic acid hydrochloride

A solution of 1.1 g (0.005 mol) of 2-acetamido-4-(hydroxymethylphosphinyl)-2-butenoic acid (Example 1a) and 10 mg (0.012 mmol) {(R,R)--P,P'-[N-benzoylpyrrolidine-3,4-diyl]bis(diphenylphosphane)}-1,5-cyclooctadienerhodium tetrafluoroborate (prepared according to European Published Application 151,282) in 60 ml of methanol prepared under nitrogen is hydrogenated in an autoclave at a pressure of 15 bar and a temperature of 30° C. while stirring. After a reaction time of 24 hours, the hydrogenation is terminated. The working up is carried out analogously to Example 2.

Yield of L-homoalanin-4-yl(methyl)phosphinic acid hydrochloride: 1.04 g (96% of theory). $[\alpha]_D^{22}=23.2°$ (c=1 in 1N HCl) corresponding to an optical yield of 90.0%.

If water is used as solvent and an H₂ pressure of 50 bar is applied, 1 g (92.3% of theory) of L-homoalanin-4-yl(methyl)phosphinic acid hydrochloride is obtained which has an angle of rotation of $[\alpha]_D^{22} = 21.9°$ (c=1 in 1N HCl) corresponding to an optical yield of 85%.

EXAMPLE 4

L-homoalanin-4-yl(methyl)phosphinic acid (a) 4.9 g (0.022 mol) of 2-acetamido-4-(hydroxymethylphosphyinyl)-2-butenoic acid (Example 1a) are suspended in a mixture of 15 ml of a glacial acetic acid and 30 ml of trimethyl orthoacetate and heated for 5 minutes under reflux. The reaction mixture is freed of all volatile constituents in high vacuum and the residue subsequently distilled in high vacuum. 4.8 g (88.4% of theory) of methyl[(3-acetamido-3-methoxycarbonyl)-2-propen-1-yl](methyl)phosphinate is obtained as a colorless oil with a boiling point of 212-15/0.0013 mbar.

(b) 0.0100 g (0.021 mmol) of chloronorbornadienerhodium(I) dimer and 0.0227 g (0.050 mmol) of (2R, 3R)-(−)-2,3,bis(diphenylphosphino)bicyclo[2.2.1]hept-5-ene (compound Vg) are dissolved under an atmosphere off argon in 5 ml of degassified methanol. The catalyst solution obtained is stirred for 15 minutes at room temprature and then added to a solution of 3.9 g (0.016 mol) of methyl [(3-acetamido-3-methoxycarbonyl)-2-propen-1-yl](methyl)phosphinate in 50 ml of methanol. The reaction vessel is evacuated, then hydrogenation is carried out at a pressure of 2.5 bar. After 3 hours the reaction is terminated. After depressurizing the reaction vessel, the reaction mixture is mixed with 2 g of acidic ion exchanger (H+ form) to remove the catalyst and stirred for 3 hours at room temperature. The ion exchanger is separated off and the reaction mixture evaporated down completely. 3.7 g (94.5% of theory) of methyl[(3-acetamido-3-methoxycarbonyl)-1-propyl](methyl)phosphinate is left as a colorless oil.

¹H-NMR (CDCl₃): δ=1.47 (d, J=14 Hz, 3H), 1.60–2.30 (m, 4H), 2.03 (s, 3H), 3.70 (d, J=10.7 Hz, 3H), 3.78 (s, 3H) 4.62 (m, 1H), 7.14 (m, broad, 1H)

(c) 2.7 g (0.0108 mol) of methyl[(3-acetamido-3-methoxycarbonyl)-1-propyl](methyl)phosphinate are dissolved in 80 ml of 6N hydrochloric acid and boiled for 15 hours under reflux. The reaction mixture is evaporated down completely and the residue left is crytallized by taking up in ethanol.

2.08 g (88.3% of theory) of L-homoalanin-4-yl(methyl)phosphinic acid hydrochloride with a melting point of 194°–96° C. (decomposes) is obtained. $[\alpha]_D^{22}$ 21.4° (c=2.02 in 1N HCl)

(d) 0.5 g (0.0023 mol) of L-homoalanin-4-yl(methyl)phosphinic acid hydrochloride are converted to the free amino acid analogously to Example 1(c).

0.4 g (96% of theory) of L-homoalanin-4-yl(methyl)phosphinic acid are obtained as a white solid with a melting point of 210°–212° C. (decomposes). $[\alpha]_D^{22} = 15.0°$ (c=1.00 in H₂O)

This corresponds to an optical yield of at least 88.2% relative to $[\alpha]_D^{23} = 17.0°$ (c=1 in H₂O) for optically pure L-homoalanin-4-yl(methyl)phosphinic acid (Sci. Reports of Meji Seika Kaisha 13, 42 (1973)).

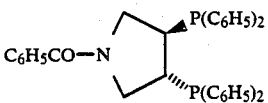

I claim:

1. A process for preparing a compound of formula I, or a salt thereof formed from an inorganic or an organic acid or base,

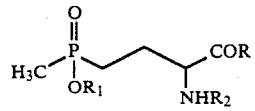

wherein
R is hydroxy, (C₁–C₆)alkoxy, Ala-Ala(—OH), Ala-Leu(OH),
R₁ is hydrogen or (C₁–C₆)alkyl, and
R₂ is hydrogen or an acyl, alkoxycarbonyl or aryloxycarbonyl radical, comprising hydrogenating a compound of formula II

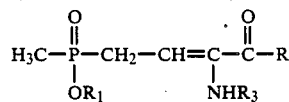

wherein
R and R₁ have the same meaning as in formula I, and
R₃ is an acyl, alkoxycarbonyl or aryloxycarbonyl radical, in the presence of a complex of formula III

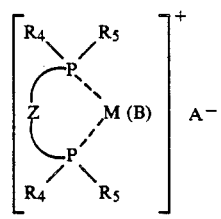

which is suitable for homogeneous asymmetric hydrogenation, where, in formula III, the R₄R₅P-Z-PR₄R₅ moiety is M is rhodium,
B is norbornadiene or cyclooctadiene and
A⁻ is an anion equivalent, and the compound of formula I, wherein R₂=R₃, so obtained is not saponified or is saponified by acidic hydrolysis into an amine hydrochloride of formula I in which R₂ is hydrogen.

2. The process as claimed in claim 1, wherein, in the compound of formula II, R₃ is a low-molecular alkanoyl or benzoyl.

3. The process as claimed in claim 1, wherein, in the compound of formula II, R is OH or (C₁–C₆) alkoxy and R₁ is hydrogen and (C₁–C₆)alkyl.

4. The process as claimed in claim 1, wherein the R₄R₅P-Z-PR₄R₅ moiety is

5. The process as claimed in claim 1, wherein the R₄R₅P-Z-PR₄R₅ moiety is

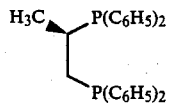

6. The process as claimed in claim 1, wherein the R₄R₅P-Z-PR₄R₅ moiety is

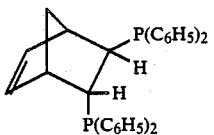

7. A process as claimed in claim 1 wherein the compound obtained after hydrogenation is saponified by acidic hydrolysis with aqueous hydrochloric acid.

8. A process as claimed in claim 7, wherein the product obtained after hydrogenation is saponified by refluxing in 6N hydrochloric acid solution.

* * * * *